(12) United States Patent
Suda et al.

(10) Patent No.: US 7,010,856 B2
(45) Date of Patent: Mar. 14, 2006

(54) LEAD WIRE ATTACHMENT METHOD, ELECTRODE, AND SPOT WELDER

(75) Inventors: Shin Suda, Tokyo (JP); Tohru Kurata, Tokyo (JP)

(73) Assignee: Nihon Kohden Corporation, Tokyo (JP)

(*) Notice: Subject to any disclaimer, the term of this patent is extended or adjusted under 35 U.S.C. 154(b) by 656 days.

(21) Appl. No.: 10/098,411

(22) Filed: Mar. 18, 2002

(65) Prior Publication Data

US 2002/0138101 A1    Sep. 26, 2002

(30) Foreign Application Priority Data

Mar. 16, 2001  (JP)  ............................ P2001-076256

(51) Int. Cl.
   *H01R 43/02*  (2006.01)

(52) U.S. Cl. .................. 29/860; 29/592.1; 29/825; 29/857; 29/876; 29/879

(58) Field of Classification Search ................ 29/878, 29/879, 874, 857, 592.1, 825, 860, 876
See application file for complete search history.

(56) References Cited

U.S. PATENT DOCUMENTS

| | | | |
|---|---|---|---|
| 3,749,101 A | | 7/1973 | Williamson |
| 5,070,608 A | * | 12/1991 | Gray .................... 29/890.044 |
| 5,867,361 A | * | 2/1999 | Wolf et al. ................ 361/302 |
| 5,870,272 A | * | 2/1999 | Seifried et al. ............ 361/302 |
| 6,031,710 A | * | 2/2000 | Wolf et al. ................ 361/302 |
| 6,049,976 A | * | 4/2000 | Khandros .................... 29/843 |

FOREIGN PATENT DOCUMENTS

| | | |
|---|---|---|
| JP | 59-501816 A | 11/1984 |
| JP | 56-45622 B2 | 7/1997 |
| WO | WO 84/01298 | 4/1984 |

* cited by examiner

*Primary Examiner*—Carl J. Arbes
(74) *Attorney, Agent, or Firm*—Sughrue Mion, PLLC

(57) ABSTRACT

A copper plate 2 is mounted on a titanium electrode element 1 by spot welding, and a lead wire 3a is attached to the copper plate 2 by solder 4.

8 Claims, 9 Drawing Sheets

LEAD WIRE ATTACHMENT METHOD, ELECTRODE, AND SPOT WELDER

BACKGROUND OF THE INVENTION

1. Field of the Invention

The present invention relates to a method of mounting a lead wire on a titanium member, an electrode having a lead wire mounted thereon by the method, and a spot welder used for manufacturing the electrode.

2. Related Art

Stainless steel, for example, has hitherto been used as an electrode element for a biomedical electrode to be used for electrically stimulating a living body from a body surface.

However, when stainless steel is used as an electrode element for electrical simulation, the following problems arise.

(1) Corrosion arises in an electrode element as a result of energization, thereby inducing dissolve of ions, such as iron ions, nickel ions, and chromium ions. As a result, the electrode element undergoes reduction in strength and deterioration in appearance.

(2) The thus-dissolved ions (particularly nickel ions and chromium ions) induce contact dermatitis or an allergic reaction.

On the contrast, if noble metal, such as gold or platinum, is used for an electrode element, dissolve of ions can be retarded. However, these substances are expensive and inappropriate for employment of high purity materials for common applications, such as a biomedical electrode.

For this reason, under another conceivable method a stainless steel electrode element is plated with gold or the like, thereby preventing dissolve of ions from the surface of the electrode element and curtailing costs. However, pits or pin holes or loss of a plating layer due to a deficiency in mechanical strength results in exposure of stainless steel, thus causing dissolve of ions by a galvanic current.

These problems have been known to be solved by use of titanium as material for the electrode element (as described in Published Japanese translation of a PCT patent publication No. 501816/1984, WO84/01298).

Titanium resists corrosion. Even when electric current is applied to titanium immersed in saline solution, a considerably small amount of ions are dissolved. For this reason, even if titanium is used as an electrode element of a biomedical electrode, it won't cause reduction in strength of the electrode or surface deterioration of the electrode.

Further, titanium is less toxic. Even if ions are dissolved, the ions will not induce contact dermatitis, poisoning, or allergic reaction. Hence, titanium is safe.

Titanium is also less expensive than gold or platinum and can be used as high-purity material for a biomedical electrode.

In contrast with stainless steel or gold, titanium cannot be soldered. Hence, when titanium is used as an electrode element, difficulty is encountered in attaching a lead wire to the electrode element. For this reason, no electrode structure in which a lead wire is readily attached to a titanium electrode element has hitherto been available, and an attachment method is complicated (as described in Examined Japanese Patent Publication No. 45622/1981 and U.S. Pat. No. 3,749,101).

SUMMARY OF INVENTION

The present invention aims at providing a method which enables easy attachment of a lead wire onto a titanium member; an electrode having a lead wire attached thereto by means of the method; and a spot welder to be used for manufacturing the electrode.

According to the present invention, a lead wire attachment method for attaching a lead wire to a first member made from titanium is provided in that a second member made from solderable material is attached to the first member by spot welding, and the lead wire is attached to the second member by soldering. As a result, sufficient strength is ensured in attaching a leadwire. Further, an electrode which dissolves a smaller amounts of ion can be manufactured at lower cost.

Preferably, one of a pair of welding electrodes to be used for spot welding is brought into contact with the first member, and a contact surface of the electrode is formed so as to become larger than a contact surface present between the first and second members. As a result, no damage arises in a contact surface between the first member and the welding electrode, which would otherwise be caused by electric spark.

Preferably, the first member is embodied as an electrode element of a biomedical electrostimulating electrode. As a result, an electrode that is safe for a living body is provided.

Preferably, the biomedical electrostimulating electrode is embodied as an electrode for electroanesthesia, urinary incontinence treatment, defibrillation, or transcutaneous electrical nerve stimulation.

When the biomedical electrostimulating electrode is embodied as an electrode for urinary incontinence treatment, the electrode element is annular, and the second member is to be attached to an interior circumferential surface of the first member.

An electrode according to the present invention comprises a first member made from titanium; a second member which is attached to the first member by spot welding and is made from solderable material; and a lead wire soldered at one end thereof to the second member. As a result, sufficient strength is ensured in attaching a lead wire. Further, ions are dissolved in a small amount, and the electrode is less expensive.

When the first member is embodied as an electrode element of a biomedical electrostimulating electrode, an electrode that is safe for a living body is obtained.

Preferably, the biomedical electrostimulating electrode is embodied as an electrode for electroanesthesia, urinary incontinence treatment, defibrillation, or transcutaneous electrical nerve stimulation.

When the biomedical electrostimulating electrode is embodied as an electrode for urinary incontinence treatment, the electrode element is annular, and the second member is to be attached to an interior circumferential surface of the first member.

A spot welder according to the present invention used in manufacturing an electrode is a spot welder comprising:

a pair of welding electrodes for clamping two members, letting current flow therebetween and welding said two members;

wherein a surface of one of said welding electrodes to contact with one of said members is sufficiently larger than that of the other welding electrode to contact with the other member so as not to cause damage by electric spark.

Further, according to the present invention, there is provided a method for welding two members with a spot welder comprising a first and a second welding electrodes for clamping said two members, letting current flow therebetween and welding said two members, wherein a surface of said first welding electrode to contact with one of said members is sufficiently larger than that of the second welding electrode to contact with the other member so as not to cause damage by electric spark, comprising steps of: clamping a titanium member and a copper plate with said first and second welding electrodes so that the surface of said first welding electrode contacts with said titanium member and the surface of said second welding electrode contacts with said copper plate; and letting current flow therebetween to welder said titanium and said copper plate.

BRIEF DESCRIPTION OF DRAWINGS

FIGS. 3A through 3C show an insertion-type electrode for urinary incontinence treatment according to the present invention, wherein

DETAILED DESCRIPTION OF PREFERRED EMBODIMENTS

Figure 1:
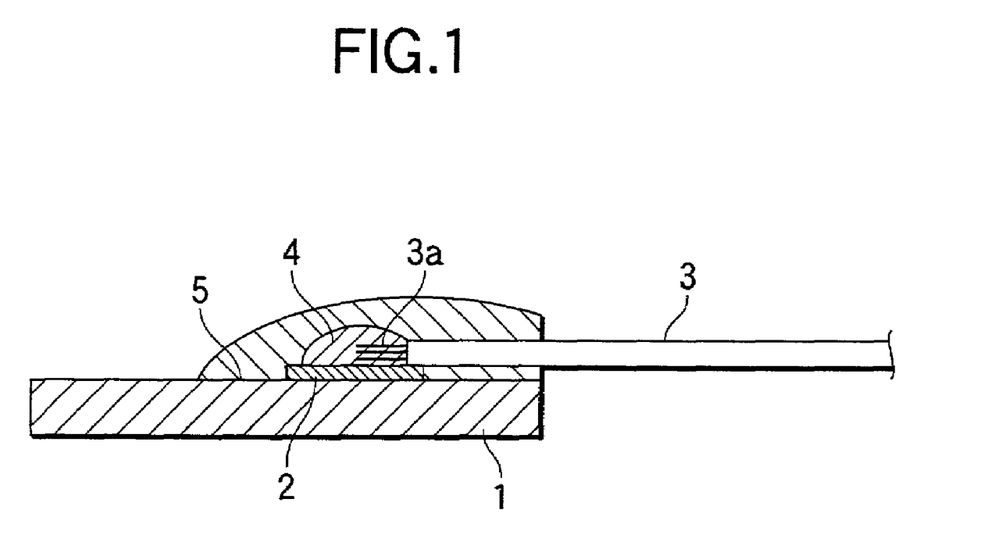
FIG. 1 shows the structure of an electrode for electroanesthesia according to the present invention.

FIG. 1 shows a basic type biomedical electrostimulating electrode according to the present invention. In the present embodiment, the electrode is to be used for electroanesthesia. An electrode element 1 employed herein is formed from titanium and assumes the shape of a disk. A copper plate 2 is mounted on top of the electrode element 1 by spot welding. One end of a conductor section 3a of a lead wire assy 3 is soldered to the top of the copper plate 2 by solder 4. The solder 4, the copper plate 2, and the end of the lead wire assy 3 are covered with an insulation section 5. For instance, epoxy resin or silicon resin is used for the insulation section 5.

In order to produce such an electrode, the copper plate 2 is mounted on the electrode element 1 by spot welding. Next, one end of the lead wire 3a of the lead wire assy 3 is soldered to the copper plate 2. Further, the solder 4, the copper plate 2, and the end of the lead wire assy 3 are coated, to thereby form the insulation section 5.

Figure 2A:
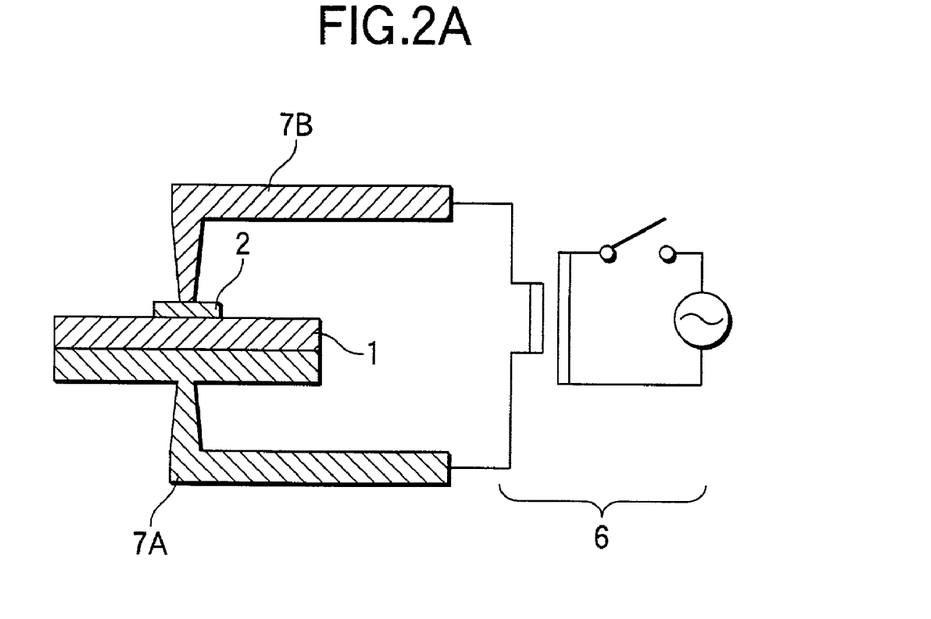
FIGS. 2A and 2B are views for describing manufacture of the electrode shown in FIG. 1.

There will now be described a welder to be used for spot-welding the copper plate 2 to the electrode element 1 during the course of manufacture of the electroanesthesia electrode. FIG. 2A is a simplified view of the welder. As illustrated, the welder has a pair of welding electrodes 7A, 7B. Electric current supplied from a supply circuit 6 flows between the electrodes 7A and 7B. A contact surface of the welding electrode 7A to be brought into contact with the electrode element 1 is set so as to become substantially identical in size with the bottom surface of the electrode element 1. Thus, the contact surface of the welding electrode 7A is formed so as to become greater in size than the surface of the electrode element 1 which comes into contact with the copper plate 2. A contact surface of the welding electrode 7B which is to be brought into contact with the copper plate 2 is made small such that electric current flows intensively into a contact point between the contact surface of the welding electrode 7B and the copper plate 2.

Figure 2B:
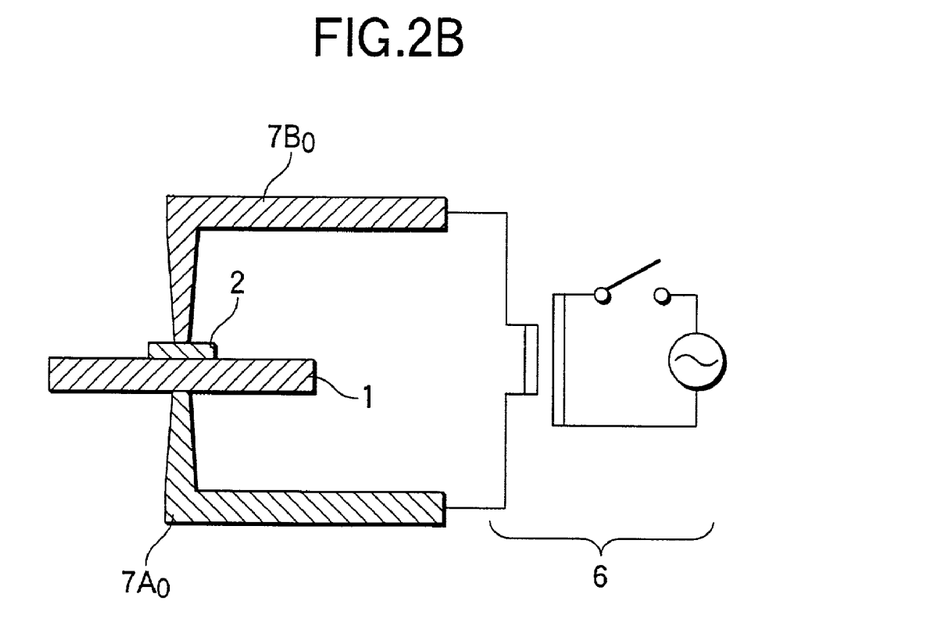

For the purpose of a comparative experiment, FIG. 2B shows an overview of a spot welder having welding electrodes whose tips are of small area. Since the contact areas of the tips to welding electrodes $7A_0$, $7B_0$ are both small, electric spark inflicts damage on the surface of the electrode element 1 which is brought into contact with the welding electrode $7A_0$. However, as shown in FIG. 2A, in the present embodiment the contact area between the welding electrode 7A and the electrode element 1 is made large. Hence, electric current flows over the entirety of the contact surface. For these reasons, electric current does not flow intensively into one point, thereby preventing occurrence of damage, which would otherwise be caused by electric spark. Hence, the exterior surface of the electrode element 1 is not impaired. Consequently, even when the electrode element 1 is attached to a living body, the contact surface of the electrode element 1 does not inflict damage to a point on the living body where the element is attached.

The electroanesthesia electrode dissolves a smaller amount of ions and hence is less likely to induce allergic reaction.

Figure 3A:
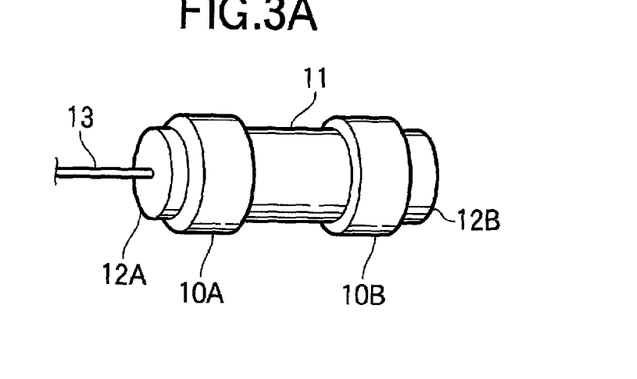
FIG. 3A is an overview of the electrode.
Figure 3B:
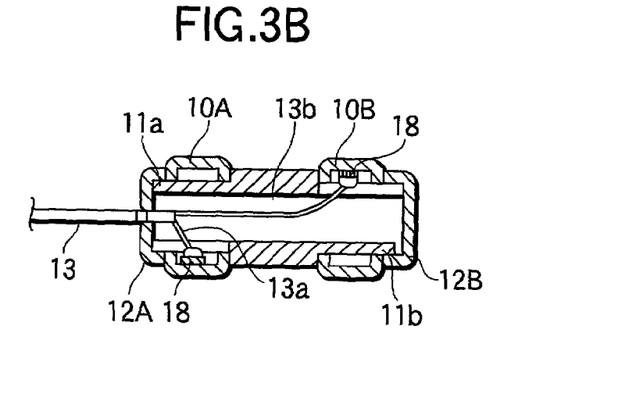
FIG. 3B is a longitudinal cross-sectional view of the electrode.
Figure 3C:
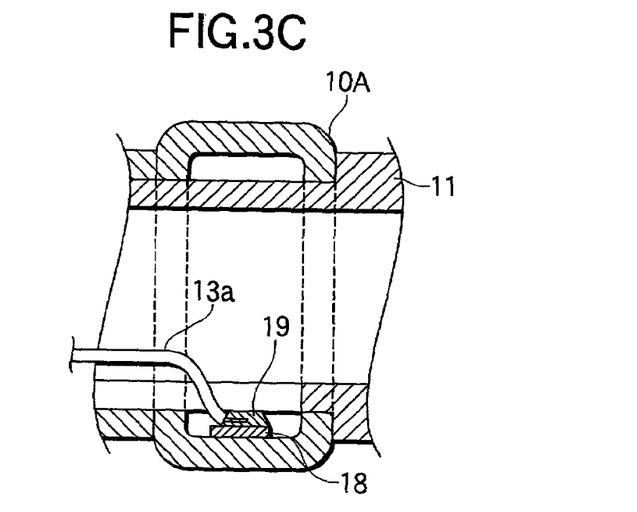
FIG. 3C is an enlarged partial view of the electrode.

FIGS. 3A through 3C show a biomedical electrostimulating electrode of insertion type according to the present invention. In this embodiment, the electrode is to be used for urinary incontinence treatment. FIG. 3A shows an overview of the entire electrode; FIG. 3B is a cross-sectional view of the electrode; and FIG. 3C is an enlarged partial view of the FIG. 3B.

As illustrated, the electrode has two annular electrode elements 10A, 10B. The electrode elements 10A, 10B are made from titanium and attached to a housing 11. The housing 11 has smaller-diameter portions 11a, 11b which extend to a predetermined width from respective ends of the housing 11 and have a smaller outer diameter. The electrode elements 10A, 10B are fitted around the respective smaller-diameter portions 11a, 11b. A cap section 12A is fitted onto the end of the smaller-diameter portion 11a, and a cap section 12B is fitted onto the end of the smaller-diameter portion 11b.

Figure 4:
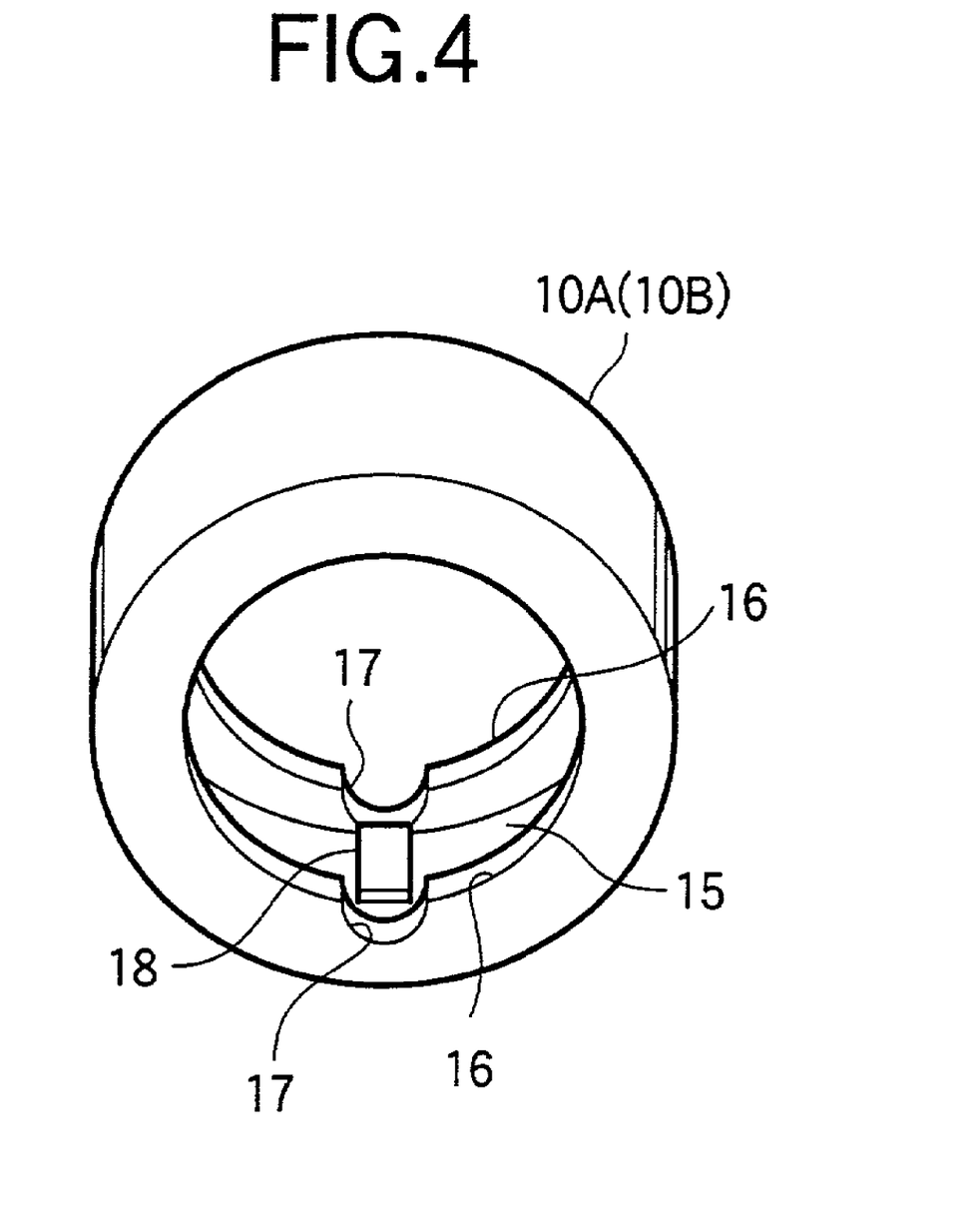
FIG. 4 shows an electrode element of the electrode shown in FIGS. 3A through 3C.

A through hole is formed in the center of the cap section 12A, and a lead wire assy 13 is inserted into the through hole. As shown in FIG. 4, a groove section 15 is formed in an interior circumferential surface of the electrode element 10A (10B). A pair of walls 16 defining the groove section 15 are partially cut away, thus forming a cutout section 17. A copper plate 18 is mounted on the bottom surface of the portion of the groove section 15 located in the vicinity of the cutout 17 by spot welding.

As shown in FIG. 3B, the lead wire assy 13 is composed of two lead wires. Among them, one lead wire 13a is at one end thereof soldered to the copper plate 18 of the electrode element 10A. One end of the other lead wire 13b is soldered to the copper plate 18 of the electrode element 10B. FIG. 3C is an enlarged view of a structure showing that the electrode element 10A and the lead wire 13a are soldered to each other. As illustrated, one end of the lead wire 13a is soldered to the copper plate 18 by solder 19.

Figure 5:
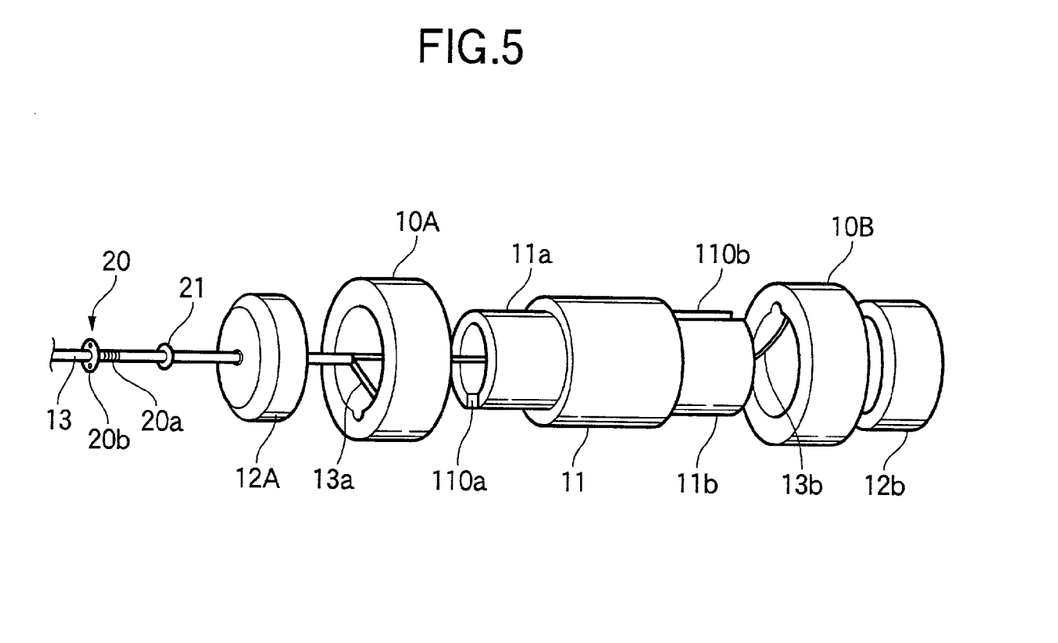
FIG. 5 is an exploded perspective view showing the electrode shown in FIGS. 3A through 3C.

FIG. 5 is an exploded perspective view of the electrode. As illustrated, a slit 110a is formed in the smaller-diameter portion 11a, and another slit 110b is formed in the smaller-diameter portion 11b. The slits 110a, 110b facilitate introduction of the lead wires 13a, 13b into the housing 11 when the electrode elements 10A, 10B are fitted around the smaller-diameter portions 11a, 11b.

The portions of the housing 11 around which the electrode elements 10A, 10B and the cap sections 12A, 12B are fitted are sealed with epoxy or silicon resin. Although the lead wire assy 13 is inserted into the through hole of the cap section 12A, the through hole is sealed with two sealing members 20, 21, into which the lead wire assy 13 is inserted. The sealing member 20 is constituted of a tube-like section 20a whose peripheral surface has threads formed thereon, and a flange section 20b attached to one end of the tube-like section 20a. The sealing member 21 is formed from an elastic material. When the tube-like section 20a of the sealing member 20 is screw-threaded into the through hole of the cap section 12A, the through hole is deformed by the flange portion 20b, thereby closing a clearance gap of the through hole. In this way, the inside of the housing 11 is sealed.

More detailed explanation will now be given of a method of attaching the lead wire 13a to the electrode element 10A.

As shown in FIG. 4, the copper plate 18 is mounted on one point on the bottom surface of the groove section 15 of the electrode element 10A by spot welding. The copper plate 18 is provided in the vicinity of the cutout section 17 so as to facilitate attachment of the lead wire 13a to the copper plate 18, which is to be performed later.

Figure 6A:
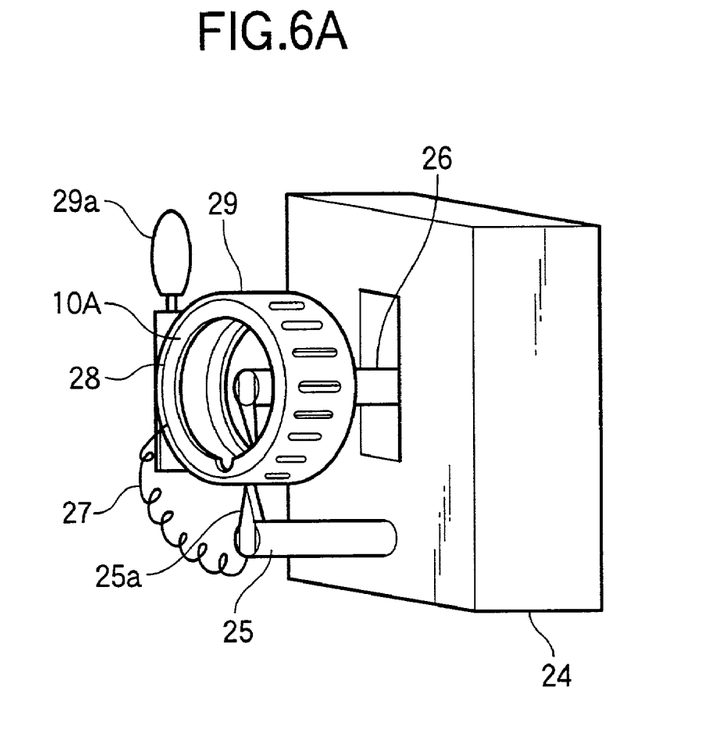
FIGS. 6A and 6B are views for describing a welder to be used for manufacturing the electrode shown in FIGS. 3A through 3C.
Figure 6B:
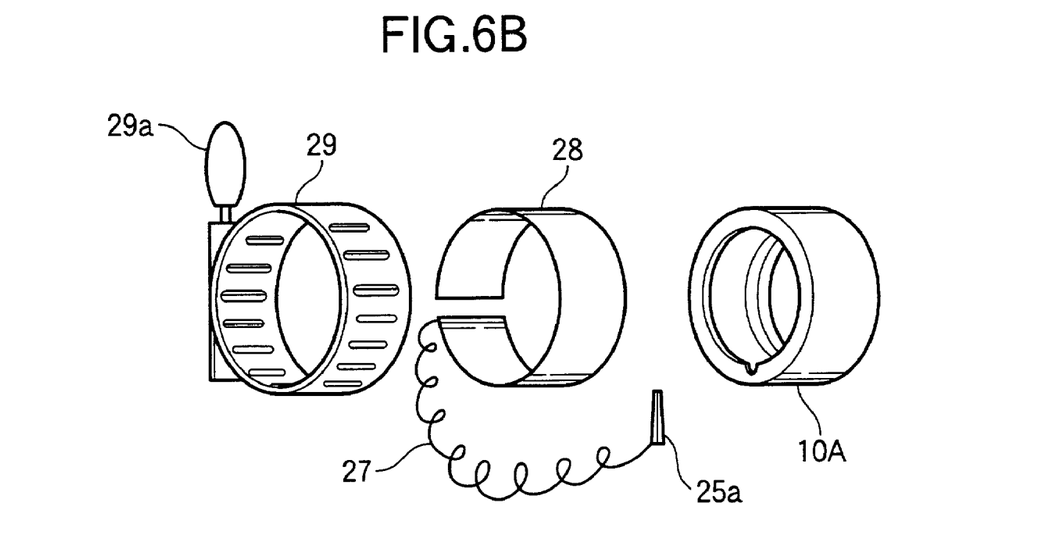

A welder shown in FIG. 6A is used for spot welding. The welder is provided with a main body 24 and a pair of welding electrodes 25, 26 projecting from the main body 24. A conductive sheet 28 bent into a substantially cylindrical shape is attached to a tip-end member 25a of the welding electrode 25 by way of a conductor 27. Further, the conductive sheet 28 is further provided with a clamp 29 which attaches the conductive sheet 28 to the outer circumferential surface of the electrode element 10A in a pressing and fastening manner with the outer circumferential surface of the electrode element 10A being covered with the conductive sheet 28. The clamp 29 has a knob 29a, and the fastening diameter of the clamp 29 can be adjusted, by turning the knob 29a. The clamp 29 is also made of a conductive member. FIG. 6B shows an exploded state of the clamp 29. As shown in FIG. 6A, a welding electrode 25 is mounted on the main body 24, whilst another welding electrode 26 is arranged so as to move vertically by switching action.

Figure 7A:
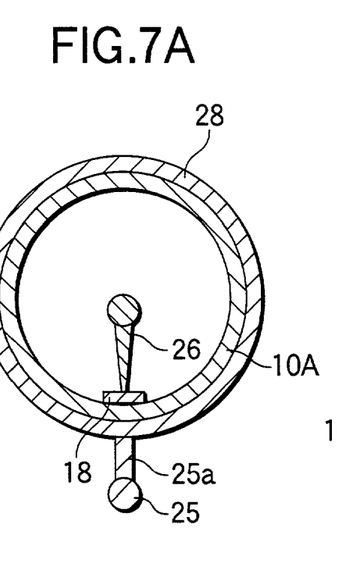
FIGS. 7A and 7B are views for describing the welder to be used for manufacturing the electrode shown in FIGS. 3A through 3C.
Figure 7B:
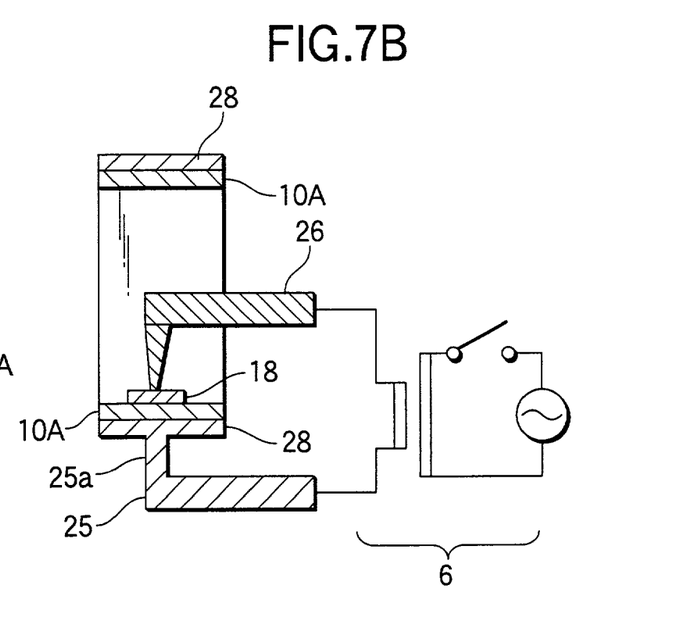

FIGS. 7A and 7B simply depict the overall configuration of the spot welder including circuits. FIG. 7A is a front cross-sectional view of the spot welder, and FIG. 7B is a side cross-sectional view of the same. Electric current flowing between the electrodes 25, 26 is supplied from the supply circuit 6. As illustrated, the electrode 25 has a conductive sheet 28 connected to a tip-end member 25a of the electrode. Since the electrode element 10A remains in intimate contact with the conductive sheet 28, a considerably large contact area exists between the electrode element 10A and the electrode 25 (the clamp 29 is omitted from FIGS. 7A and 7B).

Since a considerably large contact area exists between the electrode 25 and the electrode element 10A, spot welding prevents concentration of electric current into a narrow range on an outer circumferential surface of the electrode element 10A. For this reason, the copper plate 18 can be attached to the electrode element 10A without involvement of infliction of damage on the outer circumferential surface of the electrode element 10A, which would otherwise be caused by electric spark.

So long as the lead wire 13a of the lead wire assy 13 is soldered to the thus-attached copperplate 18, the leadwire assy 13 is attached to the electrode element 10. Although the above description relates to a method of attaching the lead wire 13a to the electrode element 10A, the same also applies to a case where the lead wire 13B is attached to the electrode element 10B.

An important factor in avoiding the infliction of damage to a living body is that the outer circumferential surface of an electrode element of the above biomedical electrostimulating electrode of insertion type is free from irregularities, such as damage caused by electric spark. The method does not cause irregularities in an electrode element during spot welding, which would otherwise be caused by electric spark. As a result, a process for smoothing irregularities is obviated, thus greatly facilitating manufacture of a biomedical electrostimulating electrode.

Since the biomedical electrostimulating electrode of insertion type dissolves a smaller amount of ions, the electrode seldom induces allergic reaction.

Figure 8A:
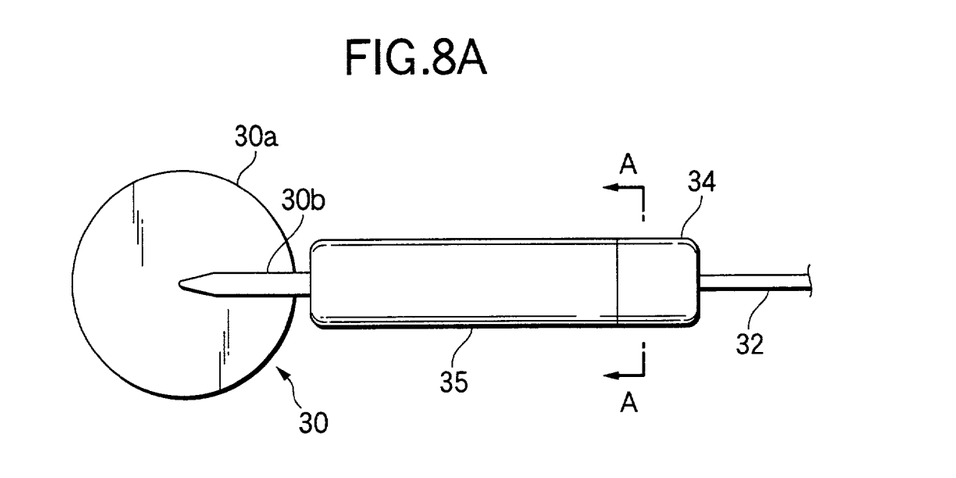
FIGS. 8A through 8C show the structure of an electrode for defibrillation according to the present invention.
Figure 8B:
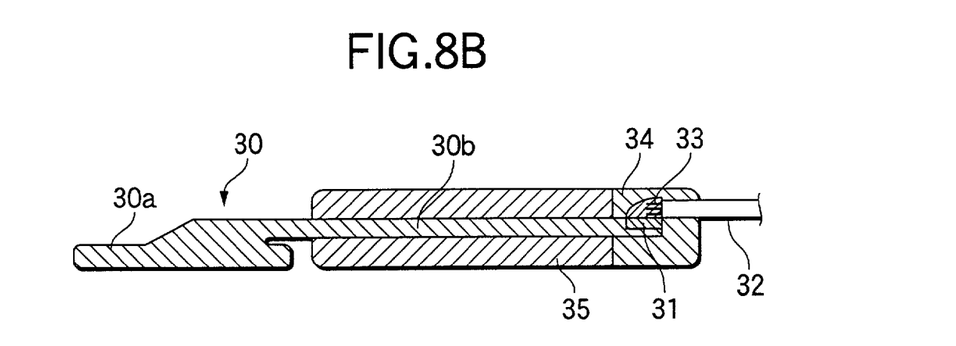
Figure 8C:
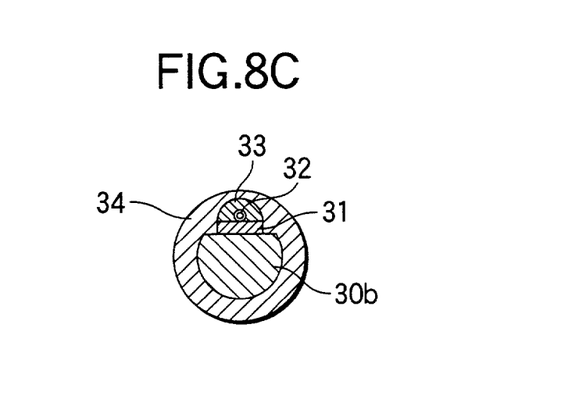

FIGS. 8A through 8C show an electrode for defibrillation according to the present invention. FIG. 8A is a plan view, FIG. 8B is a longitudinal cross-sectional view, and FIG. 8C is a cross-sectional view taken along line A—A shown in FIG. 8A. A titanium electrode element 30 is constituted of a disk-shaped electrode section 30a and a rod-shaped handle section 30b. An upper portion of the rear end of the handle section 30b is cut away, and a copper plate 31 is attached to the cutout by spot welding. As in the case of the two preceding embodiments, there is employed a spot welder having a welding electrode which is to be brought into contact with the electrode element 30 and whose contact area is larger than a contact area present between the copper plate 31 and the electrode element 30.

One end of the lead wire assy 32 is soldered to the copper plate 31 by solder 33. The solder 33, the copper plate 31, and the end of the lead wire assy 32 are covered with an insulation section 34. For instance, epoxy resin or silicon resin is used for the insulation section 34.

The entirety of the handle section 30b of the electrode element 30 is sheathed with a grip 35 made of an insulation member.

The defibrillation electrode dissolves a smaller amount of ions and hence is less likely to induce allergic reaction.

Figure 9A:
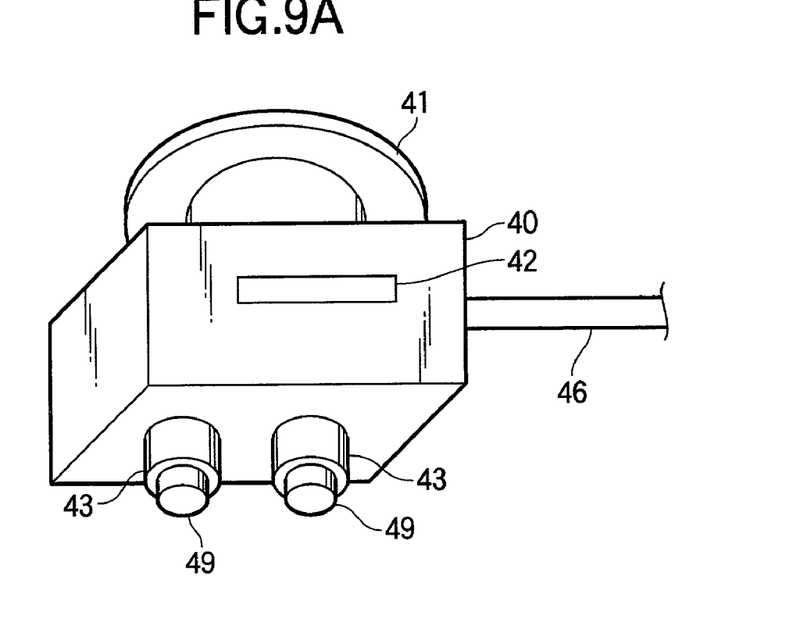
FIGS. 9A and 9B show the structure of an electrode for transcutaneous electrical nerve stimulation.
Figure 9B:
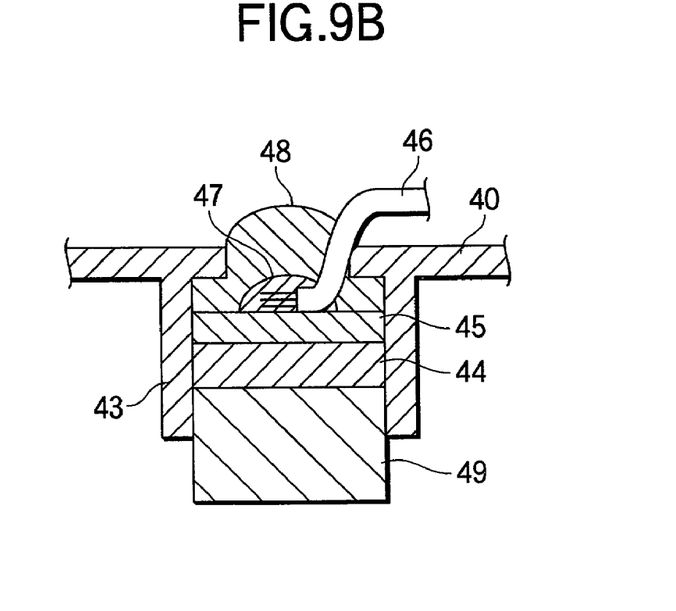

FIGS. 9A and 9B show an electrode for transcutaneous electrical nerve stimulation. FIG. 9A is an external view of the electrode, and FIG. 9B is a cross-sectional view of a portion of the electrode.

A grip 41 is provided on an upper surface of a housing 40, and a through hole section 42 for use with a strap is formed in a side surface section of the housing 40. A pair of cylindrical projections 43 are provided on the bottom surface. A disk-shaped electrode element 44 is fittingly inserted into each of the cylindrical projections 43. The electrode elements 44 are made from titanium.

A copper plate 45 is mounted on top of each of the electrode elements 44 by spot welding. As in the case of the three previously-described embodiments, there is employed a spot welder having a welding electrode which is to be brought into contact with the electrode element 44 and whose contact area is larger than a contact area present between the copper plate 45 and the electrode element 44.

One end of the lead wire assy 46 is soldered to the copper plate 45 by solder 47. The solder 47, the copper plate 45, and the end of the lead wire assy 46 are covered with an insulation section 48. For instance, epoxy resin or silicon resin is used for the insulation section 48.

A carrier 49 capable of storing an electrolyte, such as salt, dissolved in water is inserted into the inside of the extremity of the cylindrical projection 43 of the housing 40. Sponge, felt, or macromolecular gel may be used as material of the carrier 49.

According to the transcutaneous electrical nerve stimulation electrode of the present invention, small amount of ions are dissolved so that allergic reaction will be seldom induced.

The above embodiments have employed copper plates, and copper has been employed as material of a solderable member. However, silver, brass, phosphor bronze, or bronze may be used as material of a solderable member.

In addition to the above-described applications, the present invention can be applied to biological electrostimulation, such as electrostimulation for regrowth of fractured long bones or functional electrical stimulation and is not limited solely to the applications described previously.

The foregoing descriptions have been explained by referring to biomedical electrodes as embodiments. However, the present invention can also be applied to any electrode which usually has a titanium electrode element.

Since the present invention uses titanium for an electrode element, there can be provided a safe electrode which is inexpensive, has a low level of toxicity, dissolves a smaller amount of ions, and prevents occurrence of contact dermatitis, poisoning, or allergic reaction. A solderable member is attached to an electrode element by spot welding, and hence a leadwire can be mounted readily, thereby facilitating manufacture of an electrode element.

What is claimed is:

1. A method for attaching a lead wire comprising the steps of:

provided a first member made from titanium;

spot welding a second member made from solderable material to the first member; and soldering the lead wire to the second member, wherein the lead wire is electrically attached to the first member via the second member.

2. The lead wire attachment method according to claim 1, wherein one of a pair of welding electrodes to be used for spot welding is brought into contact with the first member, and a contact surface of the electrode is formed so as to become larger than a contact surface present between the first and second members.

3. The lead wire attachment method according to claim 1, wherein the first member is an electrode element of a biomedical electrostimulating electrode.

4. The lead wire attachment method according to claim 3, wherein the biomedical electrostimulating electrode is an electrode for electroanesthesia.

5. The lead wire attachment method according to claim 3, wherein the biomedical electrostimulating electrode is an electrode for urinary incontinence treatment.

6. The lead wire attachment method according to claim 5, wherein the electrode element is annular, and the second member is to be attached to an interior circumferential surface of the first member.

7. The lead wire attachment method according to claim 3, wherein the biomedical electrostimulating electrode is an electrode for defibrillation.

8. The lead wire attachment method according to claim 3, wherein the biomedical electrostimulating electrode is an electrode for transcutaneous electrical nerve stimulation.

* * * * *